(12) United States Patent
Whipple (10) Patent No.: US 9,408,714 B1
(45) Date of Patent: Aug. 9, 2016

(54) ARTIFICIAL DISC

(71) Applicant: Amendia, Inc., Marietta, GA (US)

(72) Inventor: Dale Whipple, Acworth, GA (US)

(73) Assignee: Amendia, Inc., Marietta, GA (US)

( * ) Notice: Subject to any disclaimer, the term of this patent is extended or adjusted under 35 U.S.C. 154(b) by 0 days.

(21) Appl. No.: 14/737,748

(22) Filed: Jun. 12, 2015

(51) Int. Cl.
*A61F 2/44* (2006.01)

(52) U.S. Cl.
CPC .................................. *A61F 2/4425* (2013.01)

(58) Field of Classification Search
None
See application file for complete search history.

(56) References Cited

U.S. PATENT DOCUMENTS

| | | | |
|---|---|---|---|
| 4,024,588 A | 5/1977 | Janssen et al. | |
| 5,258,031 A | 11/1993 | Salib | |
| 5,556,431 A | 9/1996 | Buttner-Janz | |
| 5,595,563 A | 1/1997 | Moisdon et al. | |
| 5,645,596 A | 7/1997 | Kim et al. | |
| 5,674,296 A | 10/1997 | Bryan et al. | |
| 6,146,421 A | 11/2000 | Gordon et al. | |
| 7,637,955 B2 | 12/2009 | Marik et al. | |
| 8,021,428 B2 | 9/2011 | Bartish et al. | |
| 8,211,179 B2 | 7/2012 | Molz et al. | |
| 8,562,682 B2 | 10/2013 | Gill et al. | |
| 8,679,182 B2 | 3/2014 | Ferree et al. | |
| 8,721,724 B2 | 5/2014 | Lechmann et al. | |
| 8,784,492 B2 | 7/2014 | Ferree et al. | |
| 8,961,608 B2 | 2/2015 | Zubok et al. | |
| 2005/0187633 A1 | 8/2005 | Ferree | |
| 2006/0079897 A1 | 4/2006 | Harrison et al. | |
| 2007/0050030 A1* | 3/2007 | Kim .................... | A61B 17/7059 623/17.11 |
| 2007/0135923 A1 | 6/2007 | Peterman et al. | |
| 2010/0234954 A1* | 9/2010 | Justis .................... | A61F 2/4425 623/17.12 |
| 2010/0298939 A1 | 11/2010 | Delfosse et al. | |
| 2012/0109306 A1 | 5/2012 | Jacob et al. | |

FOREIGN PATENT DOCUMENTS

| | | |
|---|---|---|
| CN | 103479451 | 1/2014 |
| CN | 203749650 | 8/2014 |
| JP | 03275055 | 12/1991 |

* cited by examiner

*Primary Examiner* — Sameh Boles
(74) *Attorney, Agent, or Firm* — David L. King (57) ABSTRACT

An improved artificial disc has a superior and inferior member. The superior member has an upper body portion and a flange portion for positioning and attachment to an upper vertebral body. The inferior member has a lower body portion and a flange portion for positioning and attachment to a lower vertebral body. The upper body portion and the lower body portions, when positioned in a disc space between the upper and lower vertebral bodies and affixed to a respective vertebral body at the flange portion, are independently movable relative to the other along complimentary bearing surfaces on each of the superior and inferior members. The complimentary bearing surfaces are self-aligned by a magnetic attraction force generated by at least one first permanent magnet in either the inferior or superior member.

16 Claims, 10 Drawing Sheets

ARTIFICIAL DISC

FIELD OF THE INVENTION

This application relates to an artificial prosthetic spinal disc or spinal implant device for replacing a damaged disc yet providing for mobility between the adjacent vertebrae. The implant device is particularly useful in the cervical portion of the spine and even lower where mobility of the vertebral bodies is desirably needed to be maintained.

BACKGROUND OF THE INVENTION

Intervertebral discs are soft and compressible. They are interposed between adjacent vertebral body elements of the spine. They act as shock absorbers for the spine, allowing it to flex, bend, and rotate. Degenerative disc disease can occur throughout the spine, but most often occurs in the discs in the lower back (lumbar region) and the neck (cervical region).

As the process of degeneration continues, micro tears or cracks occur in the outer layer (annulus fibrosus) of the disc. The jellylike material inside the disc (nucleus pulposus) may be forced out through the tears or cracks in the annulus, which causes the disc to bulge, break open (rupture), or break into fragments.

The economic impact of degenerative disc disease is enormous accounting for a significant morbidity and lost wages.

The physical properties of the disc are the nucleus pulposus which is composed of type II collagen and the annulus fibrosis which surrounds the disc and gives it significant form. The annulus composed of type I collagen. The nucleus pulposus is largely made up of molecules called proteoglycans. These proteoglycans have an affinity for water. It is this retention of water and the stoichiometry of folded molecules that is responsible for the unique mechanical properties of the disc. If these proteoglycans are depleted, the discs become more rigid and the loss of fluid results in a disc that is thinner and less compliant. Clinically this results in narrowing of the distances between the vertebral elements. This is best seen on magnetic resonance imaging. Typically discs have a bright signal on T2 pulse-weighted sequences and they are hypointense on corresponding T1 images. This is due to the high fluid content of the discs. As the disc loses fluid i.e. the loss of proteoglycans, the disc loses its water signal and becomes anhidrotic and eventually mineralizes. As a result, these individuals develop the symptoms in the spine contributable to loss of the normal disc architecture. As the process of degeneration continues, one develops micro tears or cracks and fissures in the annulus fibrosis and through these cracks and fissures the nucleus pulposus, which is largely gelatinous, may extrude. The extruded disc material may efface the dura and cause significant nerve compression which may result in traumatic neuritic pain and or motor loss.

Once the damage to the disc is so complete the ability to correct the problem is limited to artificial implants to restore the disc space. A more traditional approach was to use a spinal fusion implant that provided the spacing between the vertebral bodies, but thereafter allow bone growth to fuse the adjacent vertebrae together destroying any ability of these fused vertebrae to articulate.

More recently, cervical prosthetic discs have been proposed for the cervical repairs in particular ones that do not fuse the vertebral bodies, but instead allow a limited range of motion. These new articulating implant devices are a better choice until scientists can perfect disc tissue regeneration and natural biologic repair of the nucleus pulposus.

The present invention as described hereinafter is an improved spinal implant design that enhances mobility and articulation in a self-aligning and reliable construction.

SUMMARY OF THE INVENTION

An improved artificial disc has a superior and inferior member. The superior member has an upper body portion and a flange portion for positioning and attachment to an upper vertebral body. The inferior member has a lower body portion and a flange portion for positioning and attachment to a lower vertebral body. The upper body portion and the lower body portions, when positioned in a disc space between the upper and lower vertebral bodies and affixed to a respective vertebral body at the flange portion, are independently movable relative to the other along complimentary bearing surfaces on each of the superior and inferior members. The complimentary bearing surfaces are self-aligned by a magnetic attraction force generated by at least one first permanent magnet in either the inferior or superior member. The inferior or superior member opposite the member with the first permanent magnet has at least one second permanent magnet of opposing polarity relative to the at least one first permanent magnet or has a ferromagnetic composition responsive to the magnetic attractive force to self-align the complimentary bearing surfaces to a null position.

The complimentary bearing surfaces can move relative to the other in any direction by a movement of the vertebral body to which the flange is fixed. The bearing surfaces will maintain an attractive magnetic field to return to contact of the bearing surfaces upon separation during said movement. One or both of the bearing surfaces are made of a ceramic material.

In one embodiment, one of the superior or inferior members or both further has the respective upper or lower body portion formed as a two piece assembly having one base piece fixed to the flange and one movable bearing surface piece slidingly engaged to the base piece wherein the bearing surface piece can move directionally anteriorly or posteriorly relative to the base.

The bearing surfaces preferably include one convex surface and one complimentary concave surface and wherein the surfaces are translatable about the other. In another embodiment, the improved artificial disc further has an intermediate bearing layer interposed between the bearing surfaces. The intermediate bearing layer conforms to either the convex or concave surface or both. The intermediate bearing layer can be made of a compressible cushion polymer. The intermediate bearing layer also can have magnetically attachable particles intermixed in the polymer.

BRIEF DESCRIPTION OF THE DRAWINGS

The invention will be described by way of example and with reference to the accompanying drawings in which.

DETAILED DESCRIPTION OF THE INVENTION

With reference to FIGS. 1-5, a first embodiment of the present invention is illustrated. The first embodiment of the invention is an improved artificial disc assembly 10. The disc assembly 10 has a superior member 12 and an inferior member 14. The superior member 12 being configured to be attached into a disc space into an upper vertebral body. The inferior member 14 being configured to be attached into a disc space into a lower vertebral body between the two adjacent vertebral bodies. The implant 10 has main body portions 22, 24 that occupy the disc space and flange portions 23, 25 that position and allow for attachment to either the respective upper vertebral body or the lower vertebral body.

As shown, through holes 42 are provided through which the fasteners (not illustrated) can be positioned to securely attach the superior member 12 or inferior member 14 to the vertebral body to which it is to be attached. As shown, the superior member 12 has a main body portion 22 and a flange portion 23 and the inferior member 14 has a main body portion 24 and a flange portion 25. The respective through holes 42 on each side of the respective flange 23, 25 allow for the attachment of the artificial disc assembly 10 to the vertebral body to which it is to be attached.

Figure 1:
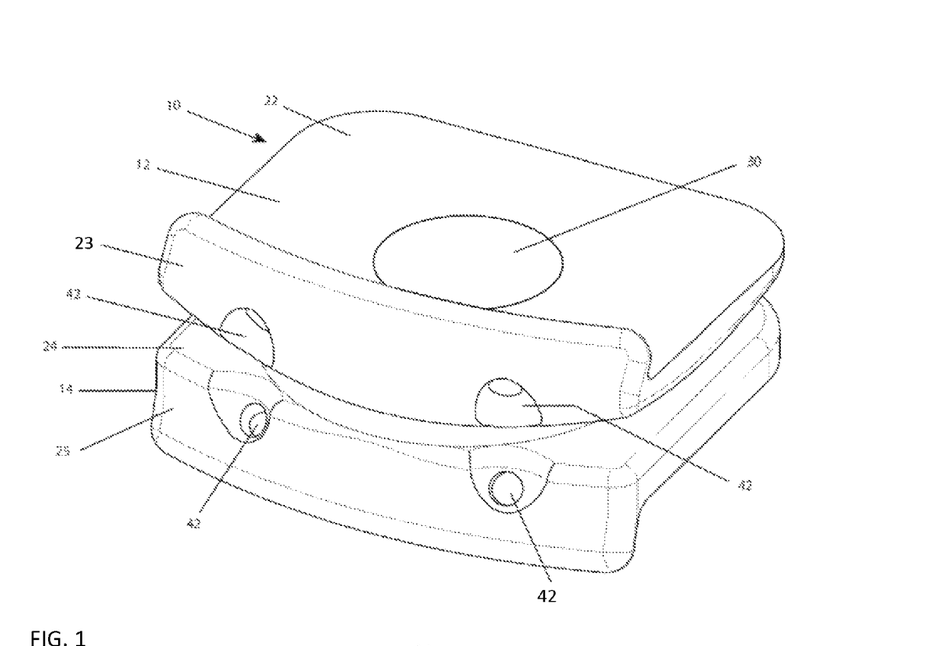
FIG. 1 is a perspective view of the implant device of the present invention.
Figure 2:
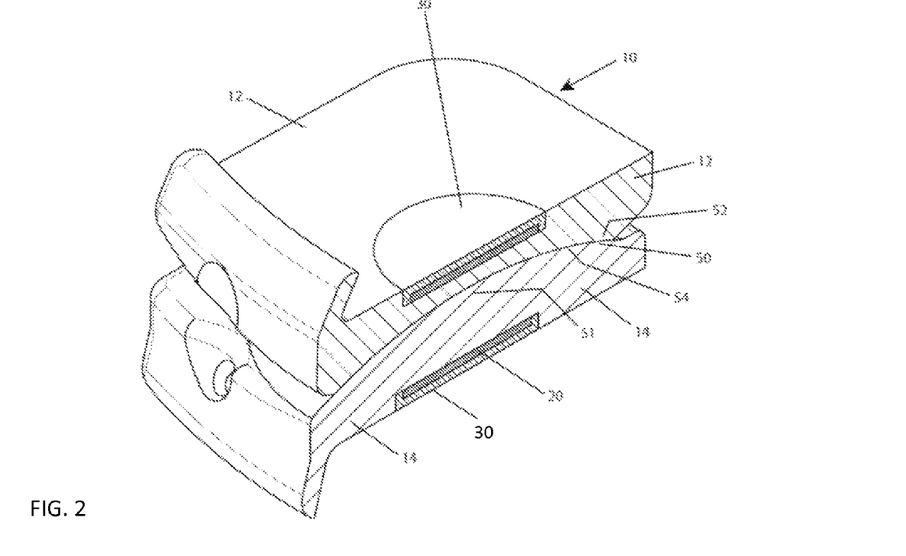
FIG. 2 is a cross-sectional perspective view of the implant device of FIG. 1.
Figure 3:
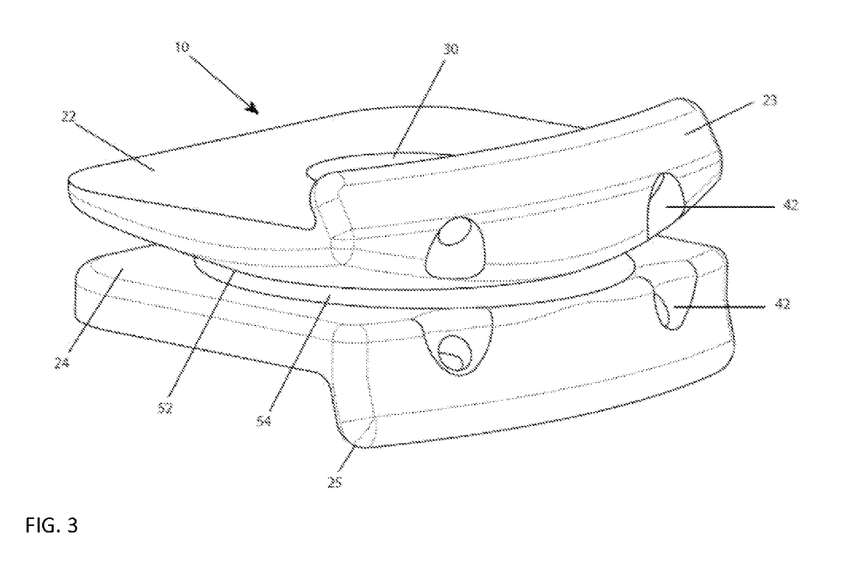
FIG. 3 is a second perspective view of the implant device of FIG. 1.
Figure 4:
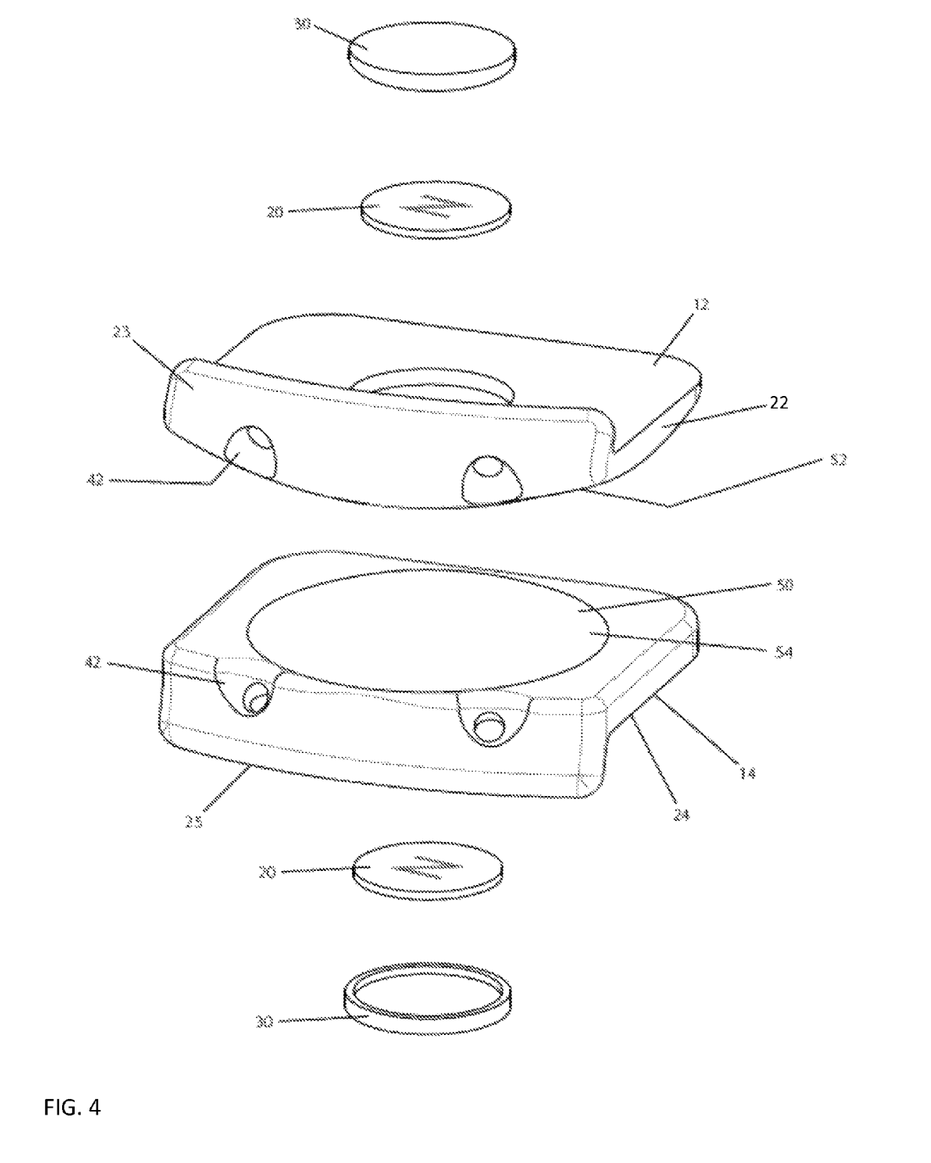
FIG. 4 is an exploded perspective view of the implant device shown in FIG. 3.
Figure 5:
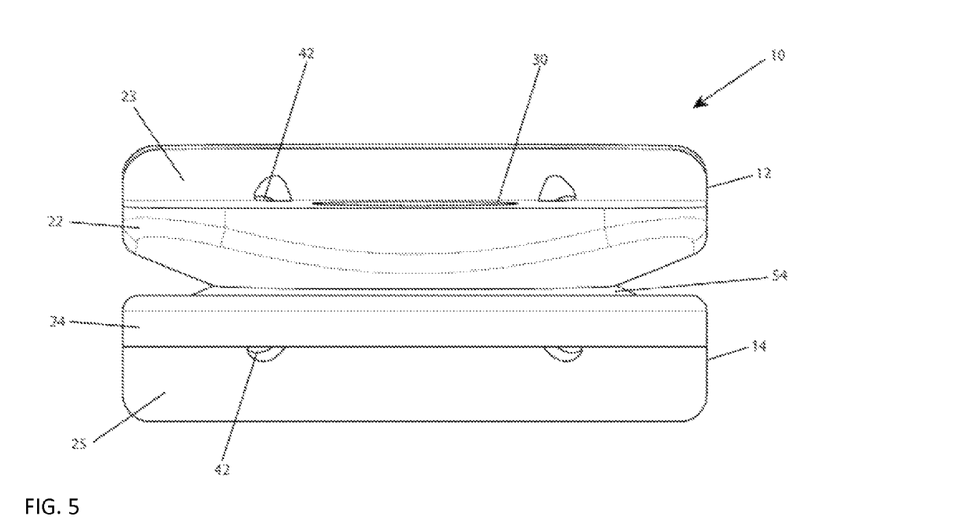
FIG. 5 is a plan view of the implant device of FIG. 1.

As shown, on the top surface of the superior member 12 is illustrated a permanent magnet 20, this permanent magnet 20 can be embedded into an opening as illustrated in cross sectional view FIG. 2. The cross sectional view of FIG. 2 shows that both the superior member 12 and inferior member 14 each have a permanent magnet 20 embedded therein. These magnets 20 shown as round disks are positioned approximately midway on the main body portion 22 or 24 of the member 12, 14 and are aligned with an apex 51 of a bearing surface 50. The bearing surfaces 50 have the superior member 12 with a circular concavity 52 and the inferior member 14 with a circular convexity 54 that provides for the ability of the superior 12 and inferior 14 members to move relative to each other with regard to the complimentary shape of the bearing surfaces 50. The artificial disc 10 is an assembly made of these two main members 12, 14 and these parts are independent, completely separate of each other overlapping at bearing surfaces 50 coupled by the attractive forces created by the permanent magnet 20 or magnets 20. The magnets 20, as shown in FIG. 4, have a North (N) and South (S) polarity so when assembled in the magnet holders 30, the upper magnet 20 has the south polarity surface (S) facing the north polarity surface (N) to insure magnetic attraction forces are generated and when in close proximity these forces are quite strong. Optionally, one or the other of the superior or inferior members 12, 14 can have the permanent magnet 20 replaced with ferromagnetic material which is responsive to magnetic fields in such a way that it can be attracted to the first permanent magnet 20 in either the superior 12 or inferior 14 member. When so constructed, it is possible for the two parts when attached to the vertebral body to open and close upon movement, for example during a cervical spine procedure, the movement of the vertebral bodies can cause the implant to want to open and separate. When this occurs, through movement of the neck, the implant can form a gap along the bearing surfaces 50. This gap is closed upon a relaxation of the neck from the moved position in such a fashion that the artificial disc implant 10 always wants to remain in the full contact position along the bearing surfaces 50 as the attractive forces pull the two parts 12, 14 together under any condition. Additionally, as shown in FIGS. 3 and 4, the artificial disc 10 may have the convex bearing surface 52 aligned with the concave bearing surface 54 in such a fashion that the two are matingly engaged. It is possible that one could rotate members 12, 14 180 degrees and have the convex surface be the upper portion and the concavity be the lower portion if so desired depending on the procedure and the location where the artificial disc 10 is to be installed.

Figure 6:
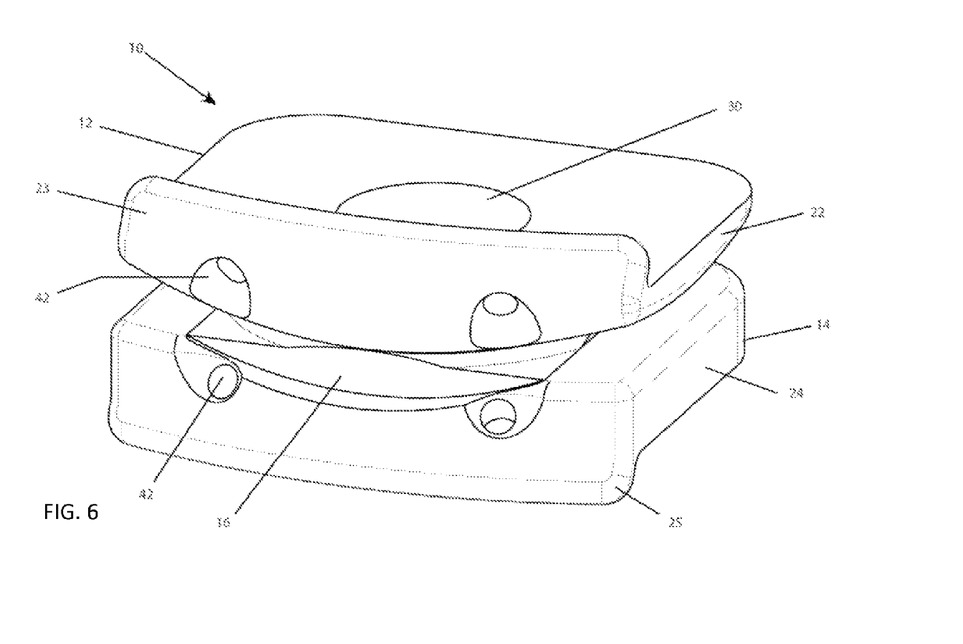
FIG. 6 is a perspective view of a first alternative embodiment of the implant device exhibiting an intermediate layer positioned between bearing surfaces.
Figure 7:
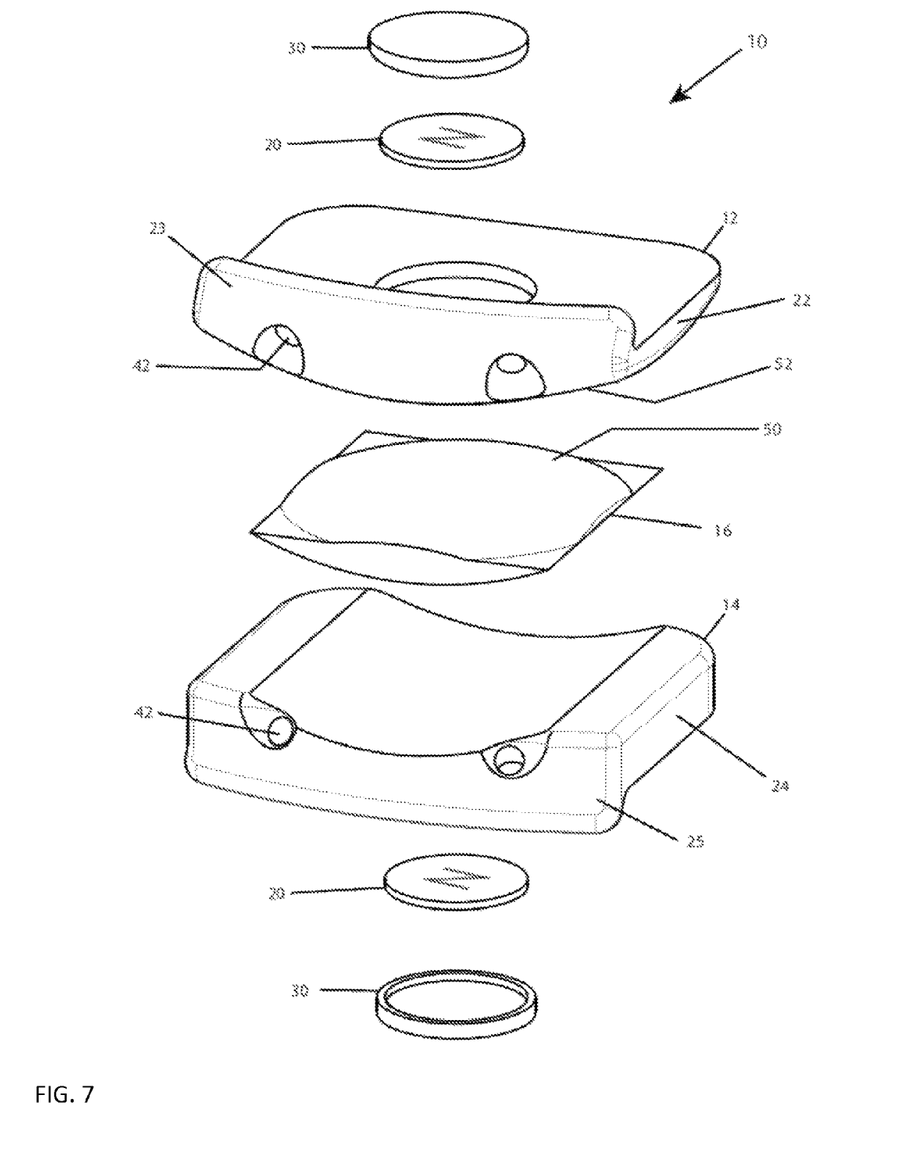
FIG. 7 is an exploded view of the first alternative embodiment of FIG. 6.
Figure 8:
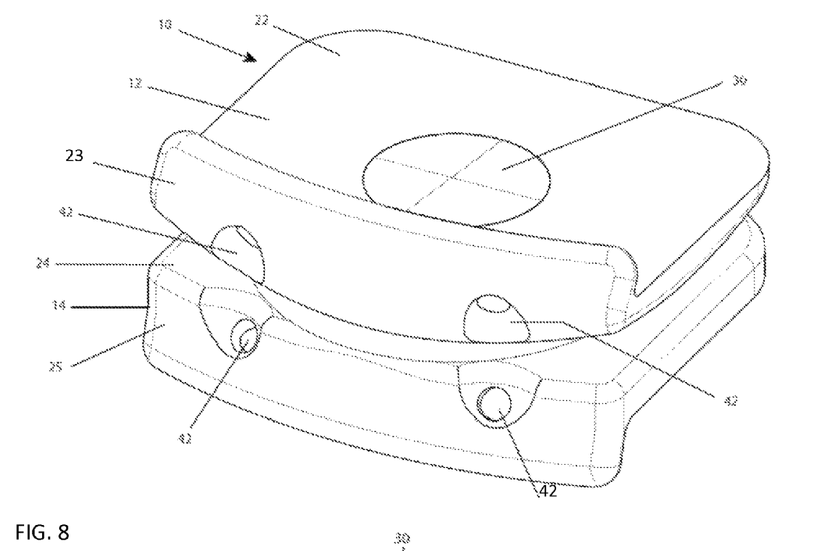
FIG. 8 is a perspective view of a second alternative embodiment of the present invention.
Figure 9:
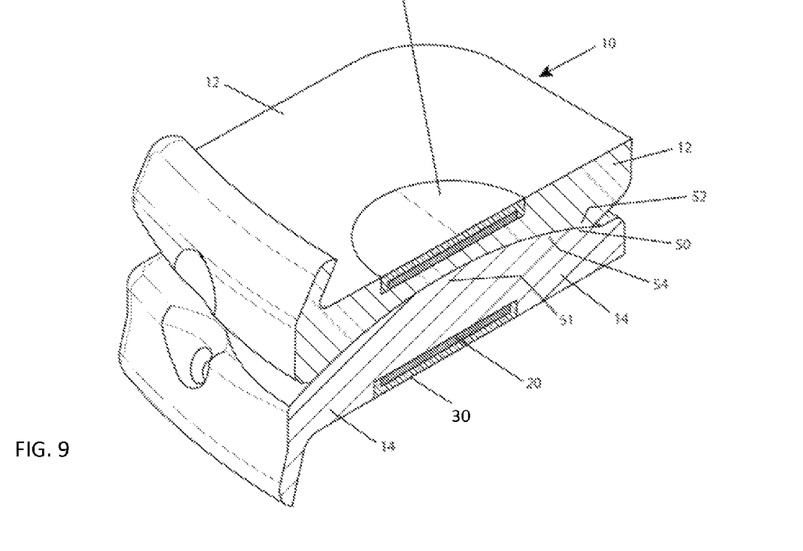
FIG. 9 is a cross-sectional perspective view of the implant device of FIG. 8.
Figure 10:
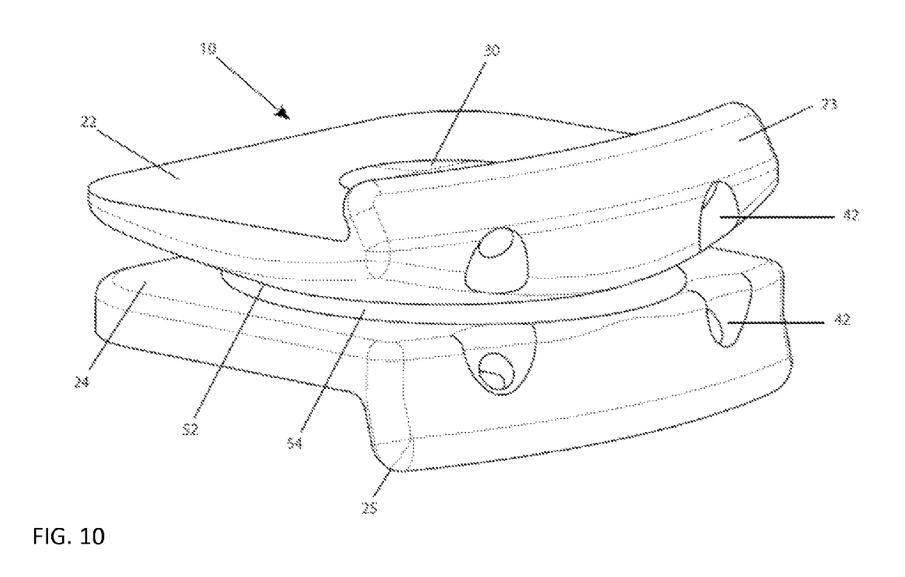
FIG. 10 is a second perspective view of the implant device of FIG. 8.
Figure 11:
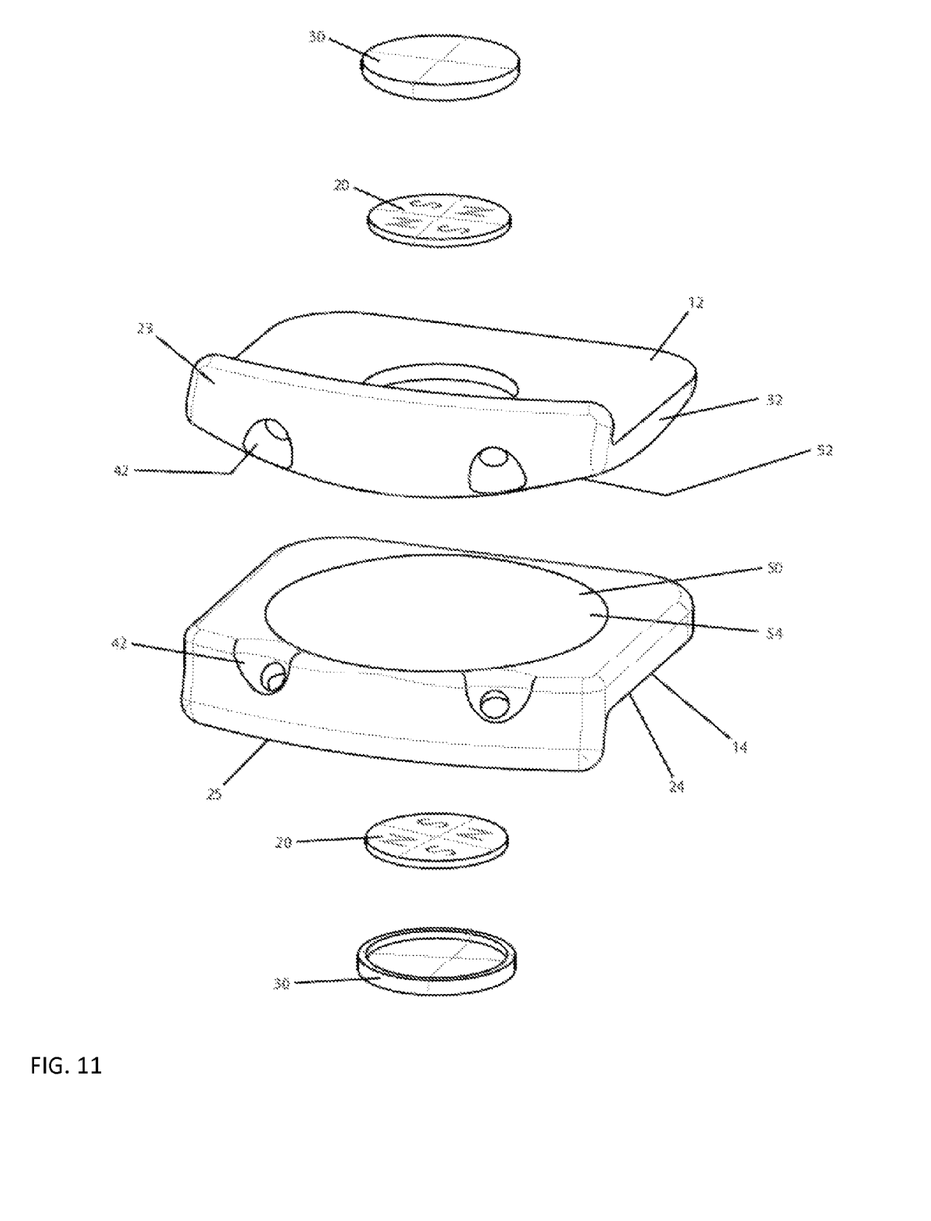
FIG. 11 is an exploded perspective view of the implant device shown in FIG. 10.
Figure 12:
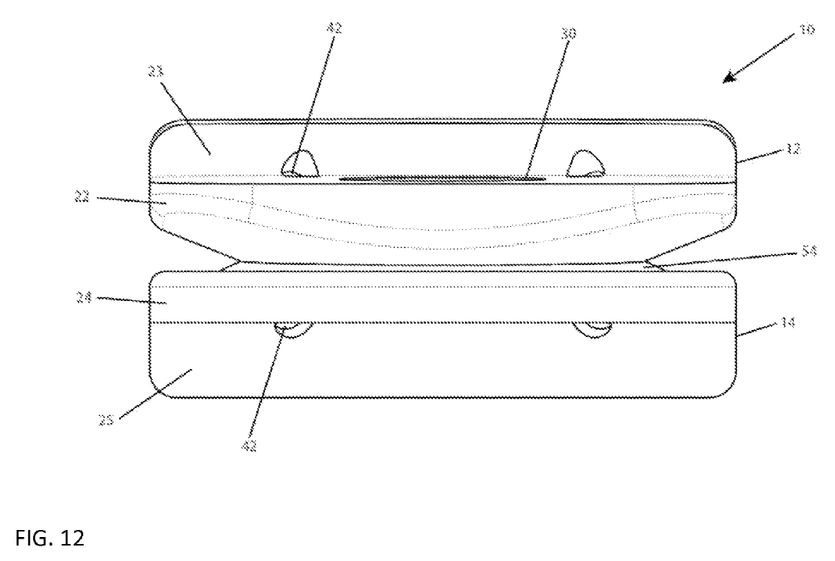
FIG. 12 is a plan view of the implant device of FIG. 8.

With reference to FIGS. 6 and 7, a first alternative embodiment is illustrated wherein the superior member 12 and the inferior member 14 have an intermediate layer 16 interposed therebetween. This intermediate layer 16 can fit in a concavity of the inferior member 14 and create the mated bearing surfaces 50 to which the superior member 12 can ride against. In such a case, the intermediate layer 16 will conform to the underlying or overlying shape and provide the necessary bearing surface upon which the two parts 12, 14 can move relative to the other and translate in any direction depending on the movement of the neck or vertebrae to which the components are attached. This relative movement allows for movement in any direction with regard to the angular rotation about an axis of the artificial disc 10 itself.

With the second alternative embodiment shown in FIGS. 8-12, all the features of the implanted artificial disc 10 are as discussed and shown in FIGS. 1-5, but with a refinement of the permanent magnets 20. As shown, the magnets 20 are used in pairs. Each magnet 20 has been divided into at least two parts, as illustrated, four parts are shown dividing the magnet 20 into four quadrants of N or S polarities. Assuming the magnet 20 has a clock face, the first quadrant is 12-3 o'clock, the second 3-6 o'clock, the third 6-9 o'clock and the fourth 9-12 o'clock. Correspondingly, the polarities on the top surface are oriented SNSN on both magnets 20, it being understood that both bottom polarities are opposites NSNS. When assembled, the upper magnet 20 will have its bottom NSNS surface facing the top of the lower magnet 20 having a SNSN surface. In this construction, the magnets 20 when aligned over the other has the same strong attractive forces holding the parts 12, 14 together, but additionally when the neck turns or moves and the magnets 20 move out of alignment, a strong repulsive force also forms as a N over N or S over S field is generated. This causes the implant 10 to move back to alignment automatically insuring not only a closure, but also a self-centering feature. As shown, with four quadrants, this can be done with two or three quadrants with great ease. Providing more than four sections creates a magnetic field diffusion that arguably is not worth the trouble and is rather inefficient in both attractive force and repulsive force generation. In this embodiment, two opposing magnets 20 are required.

Figure 13:
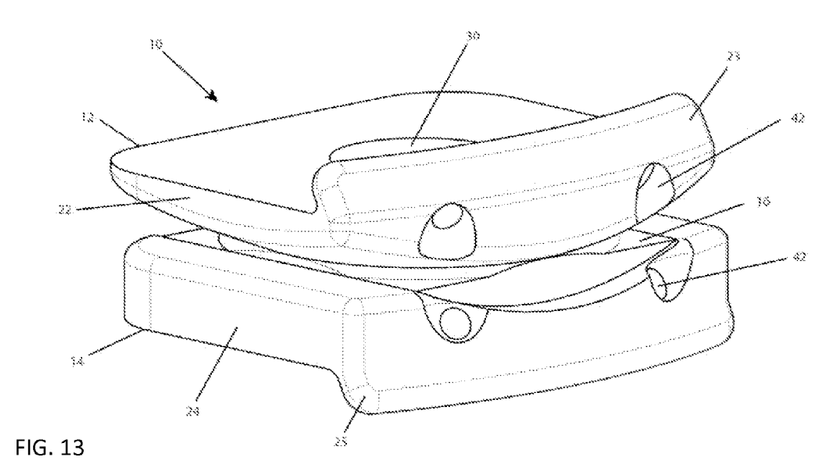
FIG. 13 is a perspective view of a third alternative embodiment exhibiting lateral translation.
Figure 14:
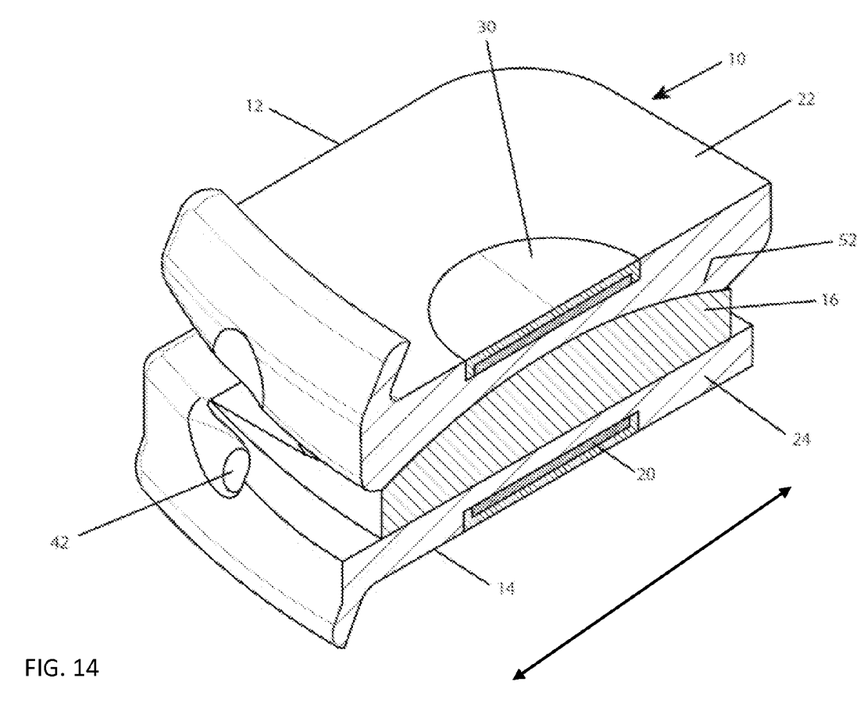
FIG. 14 is a cross-sectional view of the third alternative embodiment of FIG. 13.

With reference to FIGS. 13 and 14, this third alternative embodiment in FIG. 1-5 or 6-7 or 8-12; in any of the three previously discussed alternatives may also be provided with the capability to be able to translate anteriorly and posteriorly through a use of the one of the superior 12 or inferior 14 members having been formed in a two piece construction. Theoretically, both members 12, 14 can be made into a two piece structure, however, it is important that at least one of the members 12 or 14 have the ability to translate by being made into a two piece construction 12, 16 or 14, 16 wherein the main body portion allows a sliding intermediate portion 16 to slide in a base body portion of member 12, 14 back and forth, fore and aft or anteriorly and posteriorly so that as the neck is thrust forward or pulled back there is a slight ability to move or translate in a posterior and anterior direction without the necessity of the bearing surface 50 to be adjusted in any fashion with regard to a rotational movement. This added feature creates an additional agility of the patient to be able to maneuver his neck in a more comfortable fashion than could otherwise be achieved.

In a preferred embodiment, the members can be made at least along one or both bearing surfaces of a ceramic material for its good wear characteristics. Other parts can be made of a synthetic polymer, either with or without ferromagnetic particles or properties.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. An improved artificial disc comprises:
a superior member having an upper body portion;
an inferior member having a lower body portion; and
wherein the upper body portion and the lower body portions, when positioned in a disc space between the upper and lower vertebral bodies and affixed to a respective vertebral body, are independently movable relative to the other along complimentary bearing surfaces on each of the superior and inferior members and wherein the complimentary bearing surfaces are self-aligned by a magnetic attraction force generated by at least one first permanent magnet aligned with an apex of one of said bearing surfaces in either the inferior or superior member, wherein the bearing surfaces include one circular convex surface and one complimentary circular concave surface, the convex bearing surface aligned and matingly engaged with the concave bearing surface at the apex and wherein the bearing surfaces are translatable in any direction about the other through movement of the neck or vertebrae to which upper body and lower body portions are attached allowing for movement in any direction with regard to angular rotation about an axis of the artificial disc wherein the inferior or superior member opposite the member with the first permanent magnet has at least one second permanent magnet of opposing polarity relative to the at least one first permanent magnet or has a ferromagnetic composition responsive to the magnetic attractive force to self-align the complimentary bearing surfaces.

2. The improved artificial disc of claim 1 further comprises;
a pair of flange portions, one flange portion on the superior member for positioning and attachment to an upper vertebral body and one flange portion on the inferior member for positioning and attachment to a lower vertebral body; and
wherein the complimentary bearing surfaces can move relative to the other in any direction by a movement of the vertebral body to which the flange is fixed, the bearing surfaces will maintain an attractive magnetic field to return to contact of the bearing surfaces upon separation during said movement.

3. The improved artificial disc of claim 2 wherein one of the superior or inferior members or both further has the respective upper or lower body portion formed as a two piece assembly having one base piece fixed to the flange and one movable bearing surface piece slidingly engaged to the base piece wherein the bearing surface piece can move directionally anteriorly or posteriorly relative to the base.

4. The improved artificial disc of claim 1 wherein the inferior or superior member opposite the first permanent magnet has a ferromagnetic composition responsive to the magnetic field of the opposite member.

5. The improved artificial disc of claim 1 further comprises an intermediate bearing layer interposed between the bearing surfaces, the intermediate bearing layer conforming to either the convex or concave surface or both.

6. The improved artificial disc of claim 5 wherein the intermediate bearing layer is made of a compressible cushion polymer.

7. The improved artificial disc of claim 6 wherein the intermediate bearing layer has magnetically attachable particles intermixed in the polymer.

8. The improved artificial disc of claim 1 wherein one or both of the bearing surfaces are made of a ceramic material.

9. An improved artificial disc comprises:
a superior member having an upper body portion;
an inferior member having a lower body portion; and
wherein the upper body portion and the lower body portions, when positioned in a disc space between the upper and lower vertebral bodies and affixed to a respective vertebral body at the flange portion, are independently movable relative to the other along complimentary bearing surfaces on each of the superior and inferior members and wherein the complimentary bearing surfaces are self-aligned by a magnetic attraction force generated by two permanent magnets, one first magnet aligned with an apex of one of said bearing surfaces being in the inferior member and one second magnet of opposing polarity in the superior member, wherein the bearing surfaces include one circular convex surface and one complimentary concave circular surface, the convex bearing surface aligned and matingly engaged with the concave bearing surface at the apex and wherein the bearing surfaces are translatable in any direction about the other through movement of the neck or vertebrae to which upper body and lower body portions are attached allowing for movement in any direction with regard to angular rotation about an axis of the artificial disc wherein the inferior or superior member opposite the member with the first permanent magnet has at least one second permanent magnet of opposing polarity relative to the at least one first permanent magnet responsive to the magnetic attractive force to self-align the complimentary bearing surfaces.

10. The improved artificial disc of claim 9 wherein the first and second magnets each have at least two polarities on each top or bottom surface, the first magnet facing the second magnet with opposing polarities aligned at a centered position.

11. The improved artificial disc of claim 10 wherein the first and second magnets have three polarities on each top or bottom surface, the first magnet facing the second magnet with opposing polarities aligned at a centered position.

12. The improved artificial disc of claim 10 wherein the first and second magnets have four polarities on each top or bottom surface, the first magnet facing the second magnet with opposing polarities aligned at a centered position.

13. The improved artificial disc of claim 10 wherein a movement from a centered position generates a repulsion force to move the superior and inferior members to self-align.

14. The improved artificial disc of claim 9 wherein the inferior or superior member opposite the member with the first permanent magnet has at least one second permanent magnet of opposing polarity relative to the at least one first permanent magnet or has a ferromagnetic composition responsive to the magnetic attractive force to self-align the complimentary bearing surfaces to a null position.

15. The improved artificial disc of claim 9 further comprises;

a pair of flange portions, one flange portion on the superior member for positioning and attachment to an upper vertebral body and one flange portion on the inferior member for positioning and attachment to a lower vertebral body; and wherein the complimentary bearing surfaces can move relative to the other in any direction by a movement of the vertebral body to which the flange is fixed, the bearing surfaces will maintain an attractive magnetic field to return to contact of the bearing surfaces upon separation during said movement.

16. The improved artificial disc of claim 15 wherein one of the superior or inferior members or both further has the respective upper or lower body portion formed as a two piece assembly having one base piece fixed to the flange and one movable bearing surface piece slidingly engaged to the base piece wherein the bearing surface piece can move directionally anteriorly or posteriorly relative to the base.

\* \* \* \* \*